United States Patent [19]
Chou

[11] Patent Number: 5,586,473
[45] Date of Patent: *Dec. 24, 1996

[54] INTEGRATED NEEDLE FOR PERMANENT PIGMENT APPLICATOR

[75] Inventor: Kuei C. Chou, Taipei, Taiwan

[73] Assignee: Mei-Chi-Na Beauty International, Inc., Irvine, Calif.

[ * ] Notice: The portion of the term of this patent subsequent to Jul. 26, 2013, has been disclaimed.

[21] Appl. No.: 277,677

[22] Filed: Jul. 20, 1994

[51] Int. Cl.⁶ ........................................ B43K 5/00
[52] U.S. Cl. ........................................ 81/9.22; 606/186
[58] Field of Search ............................ 81/9.22; 606/186, 606/185

[56] References Cited

U.S. PATENT DOCUMENTS

4,914,988  4/1990  Chang ........................ 87/9.22

Primary Examiner—James G. Smith
Attorney, Agent, or Firm—Baker, Maxham, Jester & Meador

[57] ABSTRACT

An integrated needle for use with a permanent pigment applicator device having a fixed needle coupler that is coupled to a needle drive mechanism includes an elongated needle shaft with a fastening head and an attachment piece having an elongated coupling member that is detachably coupled to the needle coupler. The needle is received in a needle chamber of the attachment piece and is securely held in place around the needle fastening head. The integrated needle can be attached to the drive mechanism simply by grasping the attachment piece and coupling it to the needle coupler of the drive mechanism. After each use, the integrated needle can be disposed of and a fresh integrated needle can be attached. In this way, the needle does not have to be handled when it is attached to the applicator device and the needle coupler can be easily removed and thoroughly cleaned in an autoclave.

22 Claims, 6 Drawing Sheets

INTEGRATED NEEDLE FOR PERMANENT PIGMENT APPLICATOR

BACKGROUND OF THE INVENTION

1. Field of the Invention

This invention relates generally to the application of permanent pigment to the skin of a person and, more particularly, to devices for applying permanent pigment with a tattoo needle.

2. Description of the Related Art

Permanent pigment can be applied to the skin of a person using an applicator device and a needle with a pigment supply to provide a permanent coloration, commonly referred to as a tattoo. The applicator device generally includes a body containing a drive mechanism to which the needle is coupled. The drive mechanism can be a motor or other electromagnetic device. The needle includes a sharp pointed end and is moved along its longitudinal axis in a reciprocating motion by the drive mechanism so as to superficially puncture the skin and deposit the pigment, which is then retained permanently under the skin. Thus, the tattoo procedure exposes the needle to the tissues and blood supply of the person's body.

The needle typically is detachably coupled to the drive mechanism by a needle coupling rod that is, in turn, fixed to the drive mechanism. The coupling rod typically has a threaded end with an axial opening that receives the head of the needle. A fastening nut is tightened down over the needle and coupling rod to clamp the needle to the rod. Although the needle can be discarded after each use, usually the coupling rod is securely attached to the drive mechanism and is not accessible without virtually complete disassembly of the applicator device. It is possible for the coupling rod to come into contact with fluids and contaminants, including tissues and blood supply of different persons, as the applicator device is used on different persons. Because it cannot be readily detached from the drive mechanism, the coupling rod cannot be cleaned using acceptable sanitizing procedures, such as autoclaving. As a result, the coupling rod can contaminate a clean needle. In addition, because the fastening nut must be slipped over the needle and tightened down over the coupling rod, the needle can become contaminated merely from being handled during attachment. See, for example, U.S. Pat. No. 4,914,988 to Chang entitled Eyebrow Tattooing Machine issued Apr. 10, 1990.

It is known to provide a needle coupler between the needle and the applicator device drive mechanism. Rather than being directly attached to a drive mechanism, the needle is inserted into the needle coupler, which in turn is attached to the drive mechanism. The needle coupler holds the needle in place with a friction fit. Such an arrangement permits the drive parts that come into direct contact with the needle to be cleaned using acceptable sanitizing procedures or to be disposed of. The needle itself, however, still must be handled during attachment, providing an opportunity for contamination. In addition, inserting needles into the needle coupler can, over time, reduce the secureness of the friction fit. The needle coupler must then be replaced.

From the discussion above, it should be apparent that there is a need for an integrated needle that can be easily decoupled from a permanent pigment applicator device and that can be easily removed during normal operation and cleaned, such as in an autoclave, or disposed of, without reducing needle secureness. The present invention satisfies this need.

SUMMARY OF THE INVENTION

In accordance with the invention, an integrated needle for use with a permanent pigment applicator device having a fixed needle coupler that is coupled to a needle drive mechanism includes an elongated needle shaft with a fastening head and an attachment piece that receives the needle shaft and includes an elongated coupling member that is detachably coupled to the needle coupler. When the permanent pigment applicator device is to be used, an integrated needle can be attached to the drive mechanism simply by grasping the attachment piece and coupling it to the needle coupler of the drive mechanism. After each use, the integrated needle can be disposed of and a fresh integrated needle can be attached. In this way, the needle does not have to be handled when it is attached to the applicator device and the needle coupler can be easily removed and thoroughly cleaned in an autoclave.

In one aspect of the invention, the attachment piece of the integrated needle is internally threaded such that it can be screwed onto a threaded post of the applicator device needle coupler. This permits the integrated needle to be easily removed after use and disposed of or cleaned using commonly accepted sanitizing methods, such as an autoclave or similar device. The attachment piece preferably includes a needle chamber that receives a needle shaft and completely surrounds the fastening head portion of the needle shaft so that the needle shaft itself does not need to be handled when it is attached and detached from the applicator device. This helps reduce the chance of needle contamination during the attachment process.

In another aspect of the invention, the attachment piece comprises first and second cylindrical halves that are clamped over the needle shaft to hold it in fixed position relative to the needle chamber. The fastening head of the needle shaft may comprise a hooked end that fits into the needle chamber of the attachment piece and is thereby positively engaged with the attachment piece against longitudinal movement. Alternatively, the fastening head of the needle shaft may comprise a bulbous end that similarly fits into a needle chamber and is held in place against longitudinal movement by an internal collar of the needle chamber. In either case, the needle shaft is positively engaged with the attachment piece and is held securely in place while the applicator device reciprocates the needle shaft so as to effectuate the pigment application procedure.

Other features and advantages of the present invention should be apparent from the following description of the preferred embodiments, which illustrate, by way of example, the principles of the invention.

DESCRIPTION OF THE PREFERRED EMBODIMENTS

Figure 1:
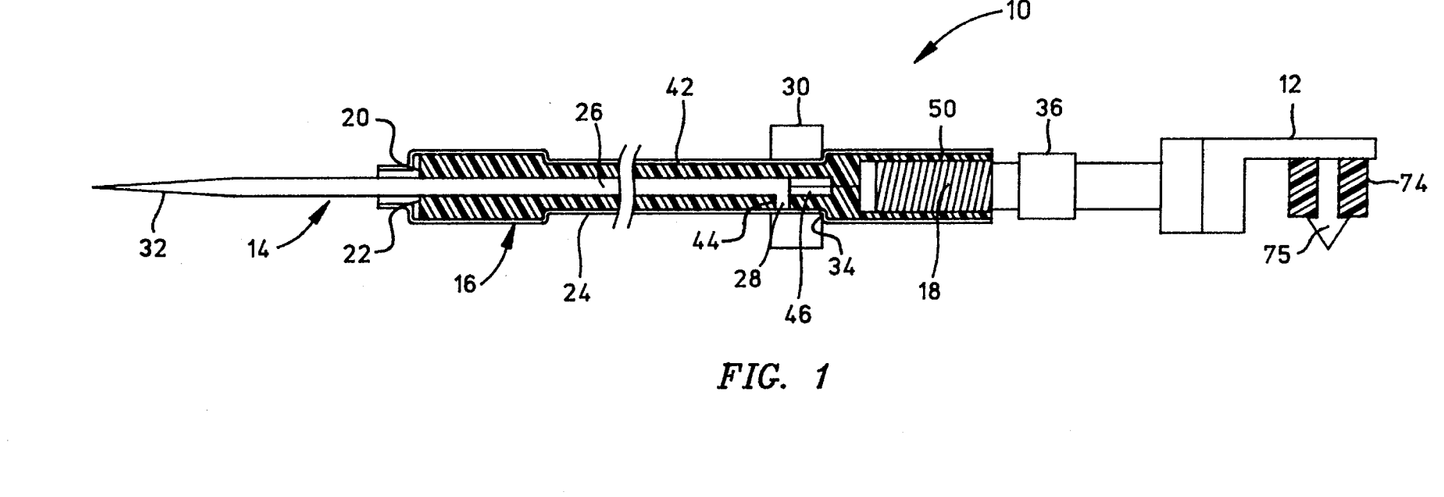
FIG. 1 is a sectional view of an integrated needle constructed in accordance with the present invention.
Figure 2:
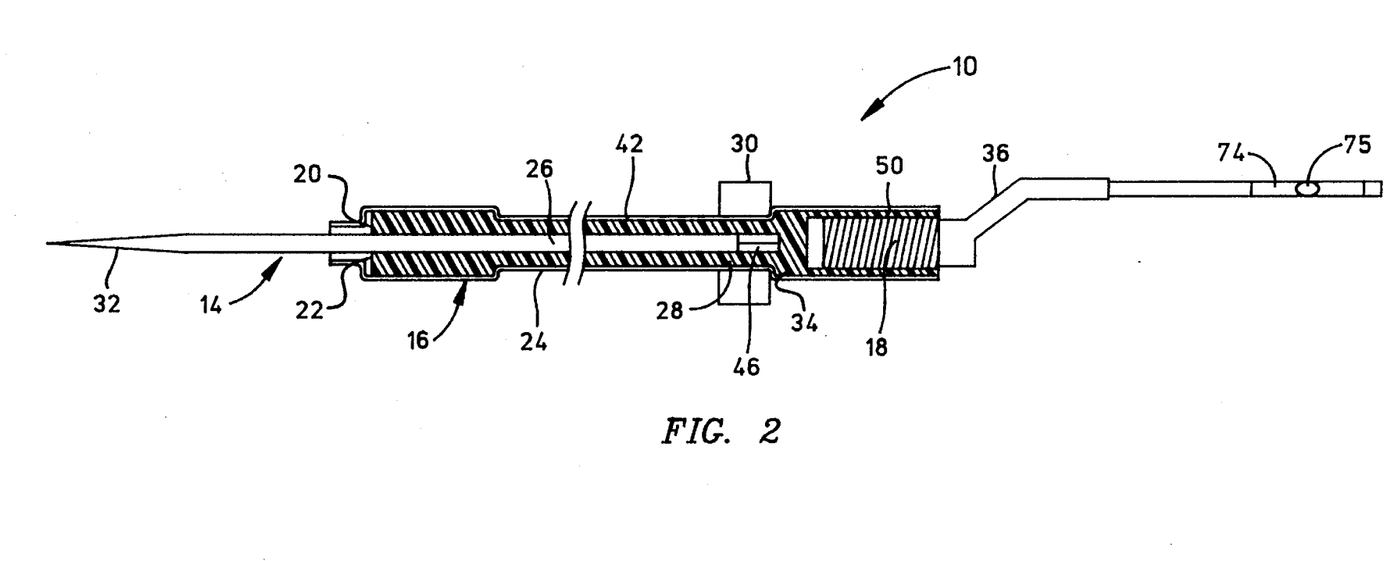
FIG. 2 is a sectional view of the integrated needle illustrated in FIG. 1, rotated along its longitudinal axis.
Figure 4:
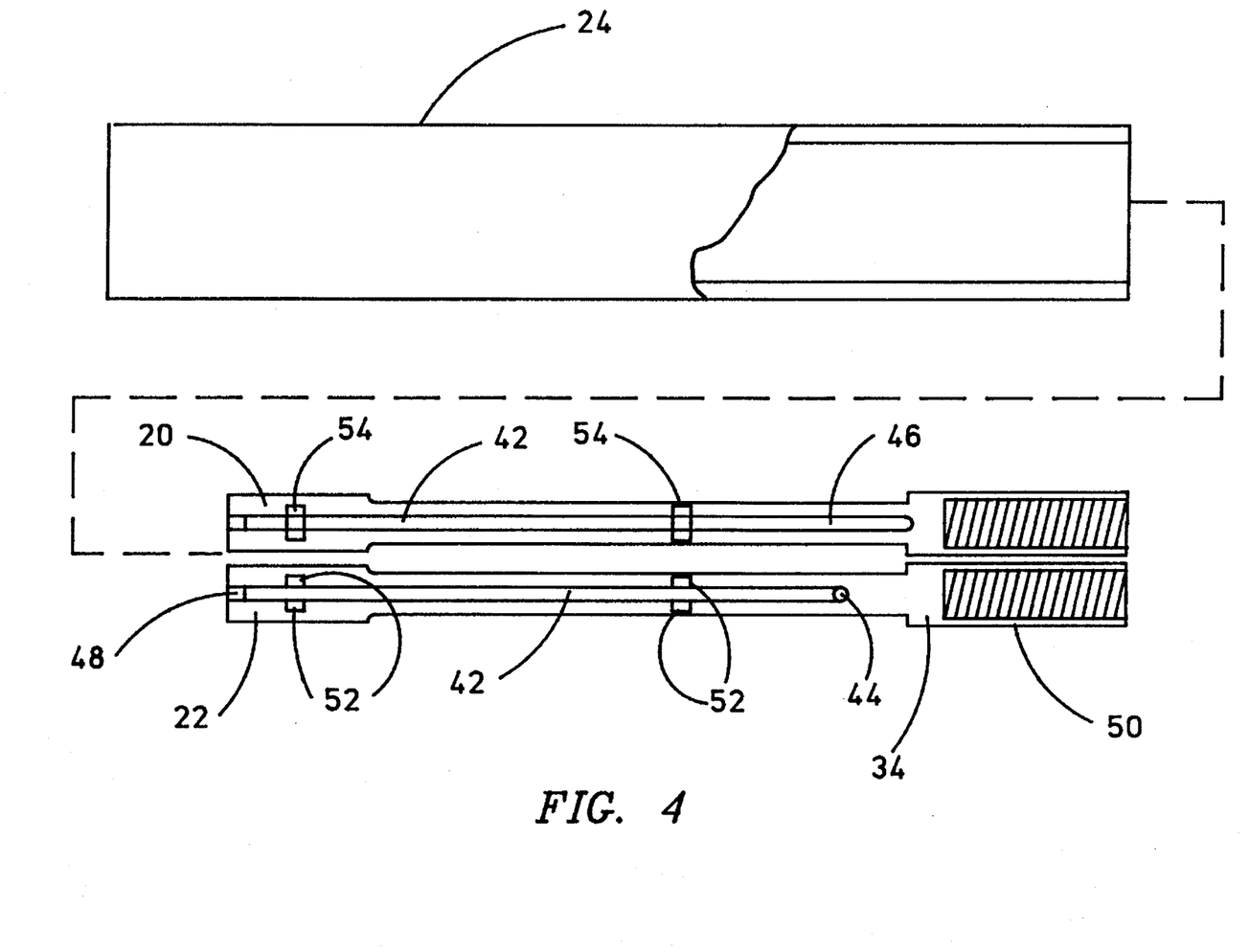
FIG. 4 is a side view of the attachment piece illustrated in FIG. 3 with the sleeve removed.

FIGS. 1 and 2 show an integrated needle 10 constructed in accordance with the present invention coupled to a needle coupler 12 of a permanent pigment applicator device (which is illustrated in greater detail in FIG. 4). The integrated needle comprises an assembly including a needle 14 and an attachment piece 16. The integrated needle can be attached to the applicator device by grasping the attachment piece 16 and screwing it onto a threaded post 18 of the needle coupler. The attachment piece comprises two half-cylinder split sections 20, 22 that, when held together by an outer sleeve 24, clamp around the needle to provide positive engagement and prevent longitudinal movement. In this way, the needle 14 does not need to be directly handled when it is attached to the needle coupler of the applicator device and is held securely against separation or ejection from the needle coupler. The needle coupler also can be easily detached from the applicator device, enabling it to be thoroughly cleaned, such as through use of an autoclave.

In the preferred embodiment, the needle 14 includes a needle shaft portion 26 and a hooked head portion 28. The needle shaft is clamped between the cylindrical portions 20 and 22 by the outer sleeve 24 and therefore is held securely in place relative to the attachment piece 16. A foam ring 30 can be placed around the outer circumference of the attachment piece. The foam ring helps to reduce travel of the pigment, or ink, upward from the tip 32 of the needle and reduces vibration of the needle, as described further below. For proper positioning of the foam ring 30, the attachment piece 16 is provided with an outer flange 34 that provides a resting surface against which the foam ring can be placed.

FIG. 2 is a view of the integrated needle 10 after it has been rotated approximately 90° about its longitudinal axis as compared with its position in FIG. 1. FIGS. 1 and 2 together show that the needle coupler 12 includes a dog-leg portion 36 that enables the needle coupler itself to be easily coupled and uncoupled from a drive mechanism of an applicator device. A needle coupler suitable for the present invention is described, for example, in greater detail in U.S. patent application Ser. No. 08/097,936 filed Jul. 26, 1993 and entitled "Permanent Pigment Applicator Having a Detachable Needle Coupler", by the present inventor, which is incorporated herein by this reference. FIGS. 1 and 2 also show respective views of the hooked head portion 28 of the needle 14.

Figure 3:
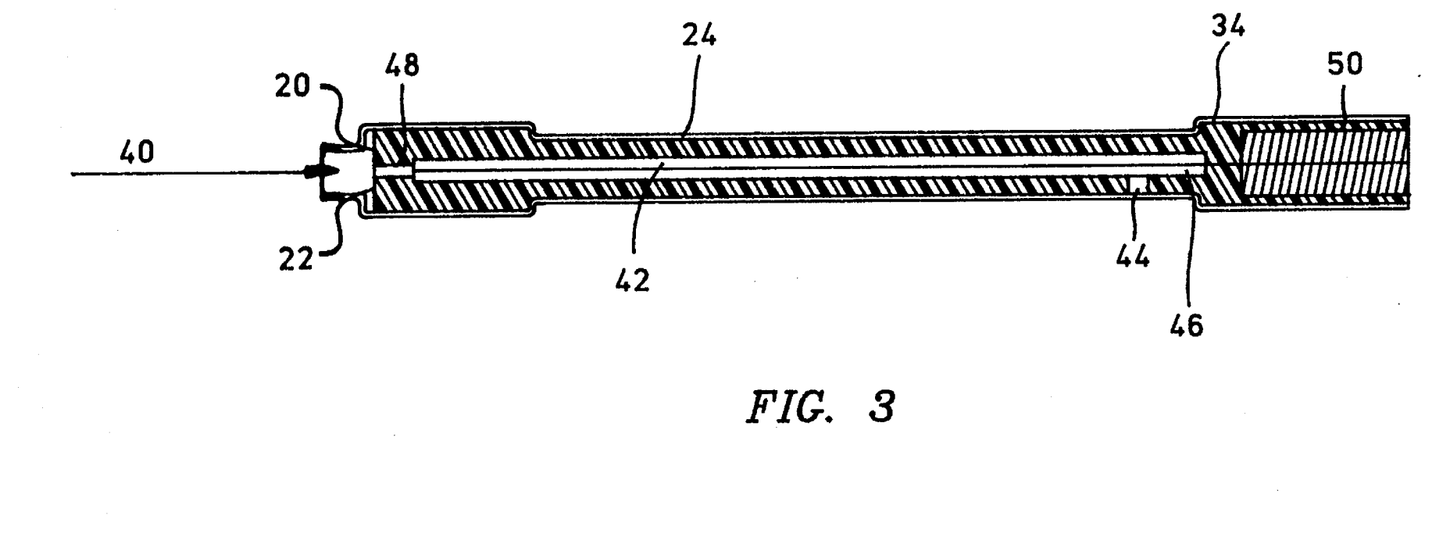
FIG. 3 is a sectional view of the attachment piece illustrated in FIG. 1 with the needle removed.

FIG. 3 is a side sectional view of the attachment piece 16 after it has been detached from the needle coupler 12 and the needle 14 has been removed. FIG. 3 shows that the attachment piece is comprised of the split sections 20 and 22 such that the split sections form a generally cylindrical needle chamber 40 that receives the needle 14. The needle chamber includes a shaft recess 42 and a lateral head recess 44. An extended portion 46 of the needle chamber permits some extra room to accommodate manufacturing variations in the length or type of needles with which the attachment piece 16 can be used. The head recess is adapted to receive the hooked end 28 of the needle and thereby hold the needle against longitudinal movement.

More particularly, the hooked end 28 of the needle 14 is held securely in the lateral recess 44 such that separation of the needle from the assembly cannot occur without shearing off the hooked end from the needle shaft. The diameter of the hooked end is selected to ensure that no shearing off occurs during normal operation or handling. In this way, the head recess 44 and the hooked end 28 of the needle 14 provide positive engagement of the needle with the attachment piece and prevent relative movement between the needle and needle coupler during operation. This type of positive engagement reduces the likelihood of needle separation or ejection during operation. A collar 48 is formed at the open end of the needle chamber. The collar fits sufficiently close around the needle shaft 26 to assist in holding the needle against movement in the needle chamber and reducing vibration.

FIGS. 1–3 show that the split sections 20, 22 are clamped around the needle shaft 26 by the outer sleeve 24, which is slipped over the split sections and thereby compresses the split sections together. The compressing of the split sections provides the positive engagement of the hooked end 28 with the head recess 44. For easier assembly, the outer sleeve is preferably constructed from a heat-shrinkable material. As known to those skilled in the art, heat-shrinkable materials change in size and pliability depending on their temperature or immersion in a solution. For example, a heat-shrinkable material at room temperature may undergo size and pliability reduction when hot air is applied to the material or when the material is removed from a solution and the solution is allowed to evaporate. FIG. 3 shows that the outer sleeve 24 extends slightly from the split sections past the internal collar 48. This provides an extra measure of security to keep the sections clamped tightly around the needle shaft.

FIG. 3 also shows that the attachment piece 16 includes a coupling member portion 50 that is internally threaded. The threads of the coupling member portion can be screwed over the threaded post 18 of the applicator device needle coupler 12. The attachment piece 16 preferably is constructed from a plastic material that provides sufficient rigidity and durability to securely hold the needle during use. The foam ring 30 can be constructed of a foam plastic. Rather than being threaded, the coupling member and applicator coupler 12 can be fit together with a snap fit. Other coupling schemes will occur to those skilled in the art.

FIG. 4 shows the attachment piece 16 with the split sections 20, 22 opened and the outer sleeve 24 removed. FIG. 4 shows the split sections after they have been rotated away from the clamped position to show the internal construction, including the needle chamber 40 and the flange 34 and coupling member 50. When the integrated needle 10 is to be assembled, the needle 14 is placed within the needle chamber such that the hooked end rests in the lateral head recess, the split sections are closed together, and the outer sleeve 24 is slipped over the split sections. When the outer sleeve undergoes its size and pliability change as part of the heat-shrink process, the outer sleeve compresses the two split sections together, thereby clamping them around the needle and securely holding the needle against longitudinal movement. This improves the action of the needle during the tattoo procedure and reduces the likelihood of needle separation or ejection from the attachment piece.

FIG. 4 also shows that the split sections 20, 22 include raised prongs 52 projecting from one split section, straddling the needle chamber 40, that are received into recesses 54 of the opposite split section. Together, the prongs and recesses increase stability of the needle and reduce vibration and movement of the needle 14 within the attachment piece 16.

Figure 5:
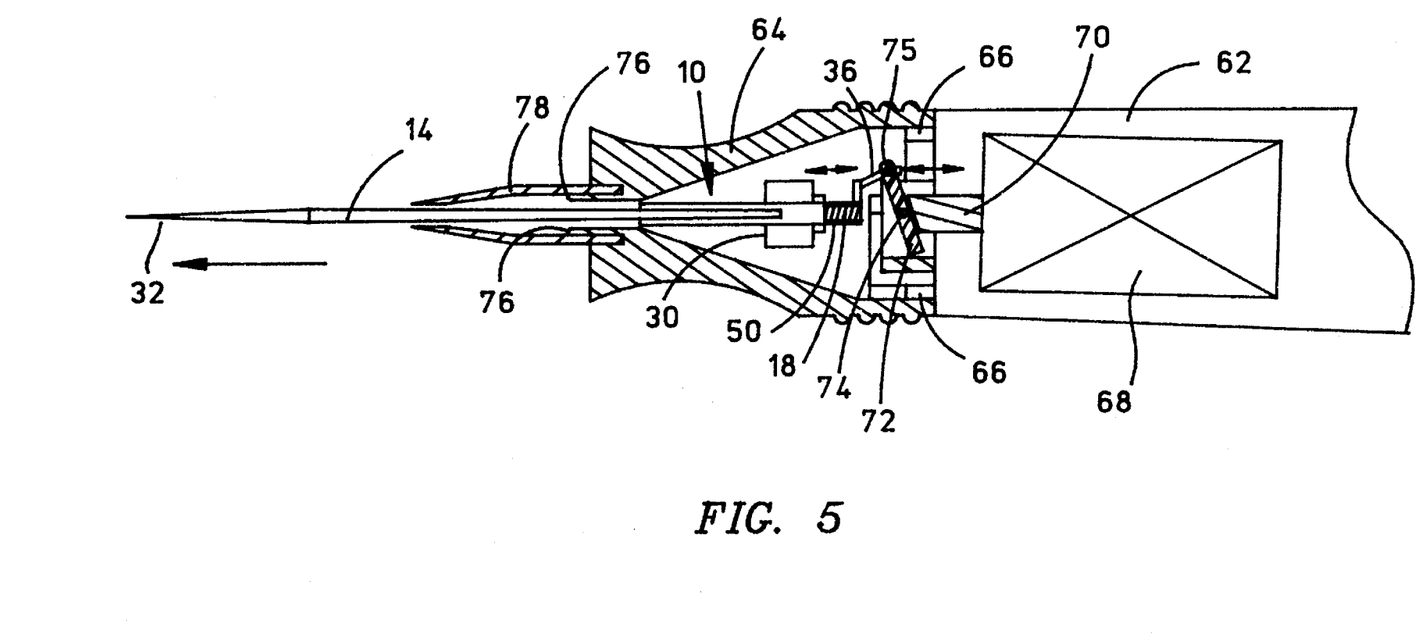
FIG. 5 is a partial sectional view showing an applicator device with the integrated needle of the present invention.

FIG. 5 shows the internal assembly of a permanent pigment applicator device 60. The applicator device includes a body portion 62 and a grip section 64, which is slidably and detachably attached to a flange 66 of the body by an interference or friction fit. Within the body 62 is a conventional drive mechanism 68, such as an electric motor.

The drive mechanism rotates a shaft 70 that in turn causes a rocker arm 72 to reciprocate about a pivot pin 74. For reduced cost and lighter weight, the rocker can be constructed of a plastic material. Other suitable drive arrangements will occur to those skilled in the art.

The particular drive mechanism of the preferred embodiment is described in greater detail in the above-referenced Ser. No. '936 U.S. patent application entitled "Permanent Pigment Applicator Having a Detachable Needle Coupler". The rocker arm 72 is pivotably coupled to the needle coupler 12 by a coupling pin 75 of the needle coupler. As described in the above-referenced patent application, the coupling pin is adapted to be coupled to the rocker arm by an interference fit so that it can be removed, if desired, from the drive mechanism in a relatively easy manner. FIG. 5 also shows that the grip section 64 includes a collar 76 and a detachable needle cup 78 that provides support to the needle 14 during its reciprocal motion and can be filled with pigment or ink. In this regard, the sponge 30 helps reduce migration of ink up the needle toward the applicator device, thereby reducing the likelihood of contamination. The sponge also moves with the needle within the grip section and provides a stabilizing mass that reduces vibration of the needle during the tattoo procedure.

Figure 6:
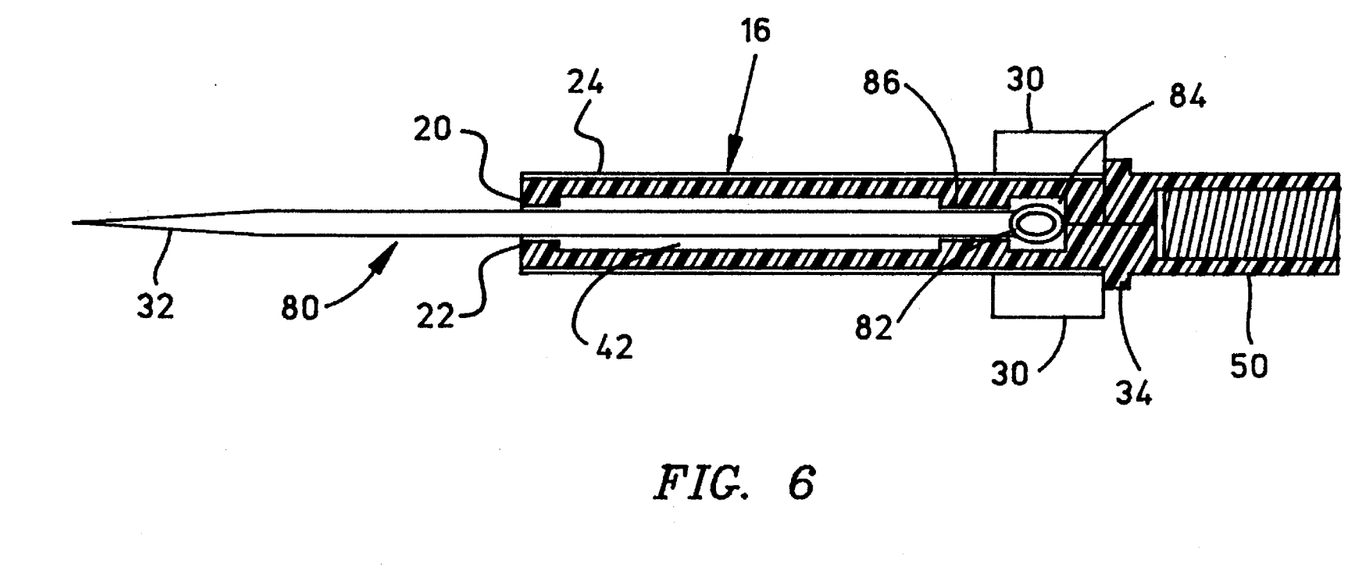
FIG. 6 is a sectional view of a second embodiment of an integrated needle constructed in accordance with the present invention.

FIG. 6 shows an alternative embodiment of a needle and attachment piece constructed in accordance with the present invention. As with the embodiment described above, the attachment piece 16 includes two split sections 20 and 22 that form a needle chamber when clamped together. In the FIG. 6 embodiment, however, the needle 80 does not have a hooked end, but, rather, has an enlarged bulbous end 82. The bulbous end is sized to fit within a head recess 84 of the needle chamber. An internal collar 86 formed by the split sections is then clamped around the needle just below the bulbous end by the outer sleeve 24 to provide positive engagement of the needle with the attachment piece. In this way, the bulbous end 82 is held securely against longitudinal movement such that separation of the needle from the assembly cannot occur without shearing off the bulbous end from the needle shaft. The diameter of the bulbous end is selected to ensure that no shearing off occurs during normal operation or handling. As with the prior embodiment described above, such a construction reduces the likelihood of needle separation or ejection from the attachment piece. The integrated needle can be attached and detached to the needle coupler 12 as described above.

Thus, an integrated needle constructed in accordance with the present invention provides a needle that can be attached and detached easily without direct handling of the needle and with reduced risk of contamination. The integrated needle includes an attachment piece that holds the needle shaft securely against longitudinal movement and ejection, thereby improving the ease with which the tattoo procedure can be carried out. The integrated needle conveniently includes a foam ring that reduces migration of pigment up the needle to the applicator device and increases stability of the needle during the tattoo procedure.

The present invention has been described above in terms of presently preferred embodiments so that an understanding of the present invention can be conveyed. There are, however, many configurations for permanent pigment applicator devices and associated needles not specifically described herein but with which the present invention is applicable. The present invention should therefore not be seen as limited to the particular embodiments described herein, but rather, it should be understood that the present invention has wide applicability with respect to applicator devices and needles generally. All modifications, variations, or equivalent arrangements that are within the scope of the attached claims should therefore be considered to be within the scope of the invention.

I claim:

1. An integrated needle for use with a permanent pigment applicator device having a needle coupler that is coupled to a needle drive mechanism, the integrated needle comprising:

a needle having an elongated shaft portion and a head at a top end; and an attachment piece that receives the needle and is detachably and coaxially coupled to the needle coupler for detachment after each use, wherein the attachment piece includes a head recess that holds the needle head, thereby preventing longitudinal movement of the needle head in the needle chamber;

wherein the head of the needle is hooked and the head recess is adapted to receive the hooked head of the needle and hold the needle head against longitudinal movement.

2. An integrated needle for use with a permanent pigment applicator device having a needle coupler that is coupled to a needle drive mechanism, the integrated needle comprising:

a needle having an elongated shaft portion and a head at a top end; and an attachment piece that receives the needle and is detachably and coaxially coupled to the needle coupler for detachment after each use, wherein the attachment piece includes a head recess that holds the needle head, thereby preventing longitudinal movement of the needle head in the needle chamber; wherein:

the head of the needle is a bulbous shape and the head recess includes a collar that clamps the needle shaft portion just below the needle head, thereby preventing longitudinal movement of the needle head in the needle chamber.

3. An integrated needle for use with a permanent pigment applicator device having a needle coupler that is coupled to a needle drive mechanism, the integrated needle comprising:

a needle having an elongated shaft portion and a head at a top end; and an attachment piece that receives the needle and is detachably and coaxially coupled to the needle coupler for detachment after each use, wherein the attachment piece includes a head recess that holds the needle head, thereby preventing longitudinal movement of the needle head in the needle chamber;

wherein the attachment piece is formed from split sections and the split sections are clamped around the needle shaft portion by the force of an outer sleeve that is slipped over the split sections and compresses the split sections together; and wherein the attachment piece includes a foam ring that fits around the outer circumference of the split sections.

4. An integrated needle as defined in claim 3, wherein the attachment piece further includes an outer flange against which the foam ring rests.

5. An integrated needle for use with a permanent pigment applicator device having a needle coupler that is coupled to a needle drive mechanism, the integrated needle comprising:

a needle having an elongated shaft portion and a head at a top end; and an attachment piece that receives the needle and is detachably and coaxially coupled to the needle coupler for detachment after each use, wherein the attachment piece includes a head recess that holds the needle head, thereby preventing longitudinal movement of the needle head in the needle chamber;

wherein the attachment piece is formed from split sections and the split sections are clamped around the needle shaft portion by the force of an outer sleeve that is slipped over the split sections and compresses the split sections together; and wherein the outer sleeve is constructed from a heat shrinkable material.

6. An integrated needle for use with a permanent pigment applicator device having a needle coupler that is coupled to a needle drive mechanism, the integrated needle comprising:

a needle having an elongated shaft portion and a head at a top end; and an attachment piece that receives the needle and is detachably and coaxially coupled to the needle coupler for detachment after each use, wherein the attachment piece includes a head recess that holds the needle head, thereby preventing longitudinal movement of the needle head in the needle chamber; wherein:

the attachment piece is formed from split sections and the split sections are clamped around the needle shaft portion by the force of an outer sleeve that is slipped over the split sections and compresses the split sections together;

the attachment piece includes a coupling member having a recess that detachably receives the needle coupler; and the coupling member recess is threaded and receives a threaded post of the needle coupler.

7. An integrated needle for use with a permanent pigment applicator device having a needle coupler, the integrated needle comprising:

a needle having a shaft and a head; and attachment means for receiving the needle and securely holding the head of the needle against longitudinal movement relative to the needle coupler and for detachably coupling to the needle coupler of the permanent pigment applicator device coaxially for detachment after each use, the attachment means comprising:

split sections that form a generally cylindrical needle chamber that receives the needle and can be closed around the needle shaft;

an outer sleeve that fits around the split sections and clamps them tightly around the needle head; and an elongated coupling member that is detachably coupled to the permanent pigment applicator device; wherein:

the needle head is hooked at one end; and the needle chamber of the attachment means includes a head recess adapted to receive the hooked head of the needle and hold the needle head against relative longitudinal movement.

8. An integrated needle as defined in claim 7, wherein:

the needle chamber includes an internal collar that is clamped around the needle shaft by the force of the outer sleeve when the outer sleeve is slipped over the split sections and thereby compresses the split sections together.

9. An integrated needle as defined in claim 8, wherein:

the coupling member of the attachment means includes a recess that detachably receives a post of the needle coupler.

10. An integrated needle as defined in claim 9, wherein:

the coupling member recess is internally threaded and the needle coupler post is externally threaded such that the coupling member recess receives the threaded post and thereby is coupled to the needle coupler.

11. An integrated needle for use with a permanent pigment applicator device having a needle coupler, the integrated needle comprising:

a needle having a shaft and a head; and attachment means for receiving the needle and securely holding the head of the needle against longitudinal movement relative to the needle coupler and for detachably coupling to the needle coupler of the permanent pigment applicator device coaxially for detachment after each use;

wherein the attachment means comprises:

split sections that form a generally cylindrical needle chamber that receives the needle and can be closed around the needle shaft;

an outer sleeve that fits around the split sections and clamps them tightly around the needle head; and an elongated coupling member that is detachably coupled to the permanent pigment applicator device; wherein:

the needle head has a bulbous shape; and the needle chamber of the attachment means includes a shaft recess and a head recess separated by an internal collar that clamps around the needle shaft just below the needle head and thereby holds the needle head so as to prevent longitudinal movement of the needle head in the needle chamber.

12. A permanent pigment applicator device comprising:

a body portion;

a drive mechanism contained substantially within the body portion;

an integrated needle including a needle having a shaft and a head, and an attachment piece that receives the needle and includes a head recess that holds the needle head, thereby preventing longitudinal movement of the needle head, the integrated needle being adapted for replacement after each application of permanent pigment and for axial coupling; and a needle coupler that is detachably coupled to the integrated needle and detachably and axially coupled to the drive mechanism;

wherein the attachment piece comprises:

a generally cylindrical needle chamber that receives the needle head; and an elongated coupling member that is detachably coupled to the needle coupler; and wherein:

the needle head is hooked at one end; and the needle chamber of the attachment piece includes a head recess that receives the hooked head of the needle and holds the needle head against longitudinal movement.

13. A permanent pigment applicator device comprising:

a body portion;

a drive mechanism contained substantially within the body portion;

an integrated needle including a needle having a shaft and a head, and an attachment piece that receives the needle and includes a head recess that holds the needle head, thereby preventing longitudinal movement of the needle head, the integrated needle being adapted for replacement after each application of permanent pigment and for axial coupling; and a needle coupler that is detachably coupled to the integrated needle and detachably and axially coupled to the drive mechanism;

wherein the attachment piece comprises:
a generally cylindrical needle chamber that receives the needle head; and
an elongated coupling member that is detachably coupled to the needle coupler; and wherein:

the needle head has a bulbous shape at one end; and the needle chamber of the attachment piece includes a shaft recess and a head recess separated by an internal collar that clamps around the needle shaft just below the needle head and holds the needle head in the needle chamber, thereby preventing longitudinal movement of the needle head in the needle chamber.

14. A permanent pigment applicator device comprising:

a body portion;

a drive mechanism contained substantially within the body portion;

an integrated needle including a needle having a shaft and a head, and an attachment piece that receives the needle and includes a head recess that holds the needle head, thereby preventing longitudinal movement of the needle head, the integrated needle being adapted for replacement after each application of permanent pigment and for axial coupling; and a needle coupler that is detachably coupled to the integrated needle and detachably and axially coupled to the drive mechanism;

wherein the attachment piece comprises:
a generally cylindrical needle chamber that receives the needle head; and
an elongated coupling member that is detachably coupled to the needle coupler; and wherein the attachment piece includes a foam ring that fits around the outer circumference of the split sections and supplies pigment to the needle shaft.

15. A permanent pigment applicator device as defined in claim 14, wherein:

the attachment piece is formed from split sections and the internal collar is clamped around the needle shaft by the force of an outer sleeve that is slipped over the split sections and thereby compresses the split sections together.

16. A permanent pigment applicator device as defined in claim 15, wherein:

the attachment piece includes a recess that detachably receives a post of the needle coupler.

17. A permanent pigment applicator device comprising:

a body portion;

a drive mechanism contained substantially within the body portion;

an integrated needle including a needle having a shaft and a head, and an attachment piece that receives the needle and includes a head recess that holds the needle head, thereby preventing longitudinal movement of the needle head, the integrated needle being adapted for replacement after each application of permanent pigment and for axial coupling; and a needle coupler that is detachably coupled to the integrated needle mad detachably and axially coupled to the drive mechanism;

wherein the attachment piece includes a recess that detachably receives a post of the needle coupler; and wherein the attachment piece recess is internally threaded and the needle coupler post is externally threaded such that the attachment piece recess receives the threaded post and thereby is coupled to the needle coupler.

18. A permanent pigment applicator device comprising:

a body portion;

a drive mechanism contained substantially within the body;

an integrated needle including a needle having a shaft and a head, and an attachment piece that receives the needle and includes a head recess that holds the needle head, thereby preventing longitudinal movement of the needle head, the integrated needle being adapted for replacement after each application of permanent pigment and for axial coupling; and a needle coupler that is detachably coupled to the integrated needle and detachably and axially coupled to the drive mechanism;

wherein the needle coupler includes a coupling pin that is received by the drive mechanism and thereby detachably couples the needle coupler to the drive mechanism.

19. A permanent pigment applicator device as defined in claim 18, wherein the coupling pin is received in an eye of the drive mechanism to define a pivot axis and includes an enlarged end that provides an interference fit between the coupling pin and the drive mechanism so that the needle coupler is releasably held in engagement with the drive mechanism and can pivot about the pivot axis without disengaging from the drive mechanism.

20. A permanent pigment applicator device as defined in claim 19, wherein the drive mechanism includes a rocker assembly having a rocker that is pivotally supported by a rocker pin and contains the pin-receiving eye.

21. A permanent pigment applicator device as defined in claim 20, wherein the axis of the rocker pin is parallel to the axis of the needle coupler coupling pin.

22. A permanent pigment applicator device as defined in claim 21, wherein the rocker assembly is constructed from a plastic material.

\* \* \* \* \*